US009138133B2

(12) United States Patent
Breedveld et al.

(10) Patent No.: US 9,138,133 B2
(45) Date of Patent: Sep. 22, 2015

(54) INSTRUMENT FOR FINE-MECHANICAL OR SURGICAL APPLICATIONS

(75) Inventors: Paul Breedveld, Gouda (NL); Jules Serge Scheltes, Amsterdam (NL)

(73) Assignee: Technische Universiteit Delft (NL)

( * ) Notice: Subject to any disclaimer, the term of this patent is extended or adjusted under 35 U.S.C. 154(b) by 2531 days.

(21) Appl. No.: 10/597,186

(22) PCT Filed: Jan. 5, 2005

(86) PCT No.: PCT/NL2005/000001
§ 371 (c)(1),
(2), (4) Date: Apr. 18, 2008

(87) PCT Pub. No.: WO2005/067785
PCT Pub. Date: Jul. 28, 2005

(65) Prior Publication Data
US 2008/0234545 A1    Sep. 25, 2008

(30) Foreign Application Priority Data
Jan. 16, 2004    (NL) ...................................... 1025274

(51) Int. Cl.
| A61B 1/04 | (2006.01) |
| A61B 1/00 | (2006.01) |
| A61M 25/00 | (2006.01) |
| A61B 17/00 | (2006.01) |
| A61B 1/005 | (2006.01) |
| A61B 17/29 | (2006.01) |
| A61B 1/05 | (2006.01) |

(52) U.S. Cl.
CPC .............. *A61B 1/0055* (2013.01); *A61B 17/29* (2013.01); *A61M 25/0054* (2013.01); *A61B 1/05* (2013.01); *A61B 2017/003* (2013.01); *A61B 2017/00305* (2013.01); *A61B 2017/291* (2013.01); *A61B 2017/2905* (2013.01)

(58) Field of Classification Search
USPC .............. 600/114, 127–130, 139–152; 606/1, 606/205–209; 604/523–528
See application file for complete search history.

(56) References Cited

U.S. PATENT DOCUMENTS

| 3,498,286 | A |   | 3/1970 | Polanyi et al. | |
| 3,590,232 | A | * | 6/1971 | Sadowski | ...................... 362/573 |
| 4,149,391 | A |   | 4/1979 | Driver | |
| 5,085,283 | A | * | 2/1992 | Seabourn et al. | .............. 175/61 |
| 5,372,587 | A |   | 12/1994 | Hammerslag et al. | |
| 7,117,703 | B2 | * | 10/2006 | Kato et al. | ...................... 72/135 |
| 2002/0177750 | A1 |   | 11/2002 | Pilvisto | |
| 2003/0045778 | A1 | * | 3/2003 | Ohline et al. | ................. 600/114 |
| 2008/0086854 | A1 | * | 4/2008 | Boyd et al. | ................... 24/715.3 |

FOREIGN PATENT DOCUMENTS

| DE | 28 20 239 A1 | 11/1978 |
| WO | WO 93/23111 A1 | 11/1993 |
| WO | WO 02/13682 A1 | 2/2002 |

* cited by examiner

*Primary Examiner* — Ryan Henderson
(74) *Attorney, Agent, or Firm* — Akerman LLP

(57) ABSTRACT

The invention relates to an instrument for high-precision or surgical applications of a minimally invasive nature, comprising a distally positioned directable head, a shaft upon which the head is positioned, and a proximally positioned handgrip for operating the head, wherein a ring of cables comprising longitudinally extending cables connects to the head, wherein each cable of the ring of cables is disposed such that at least a part of both sides is in direct contact with another cable of the ring of cables, and wherein the cables are fixedly secured in the radial direction.

15 Claims, 4 Drawing Sheets

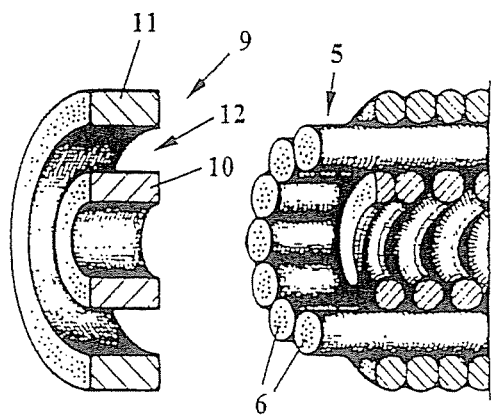
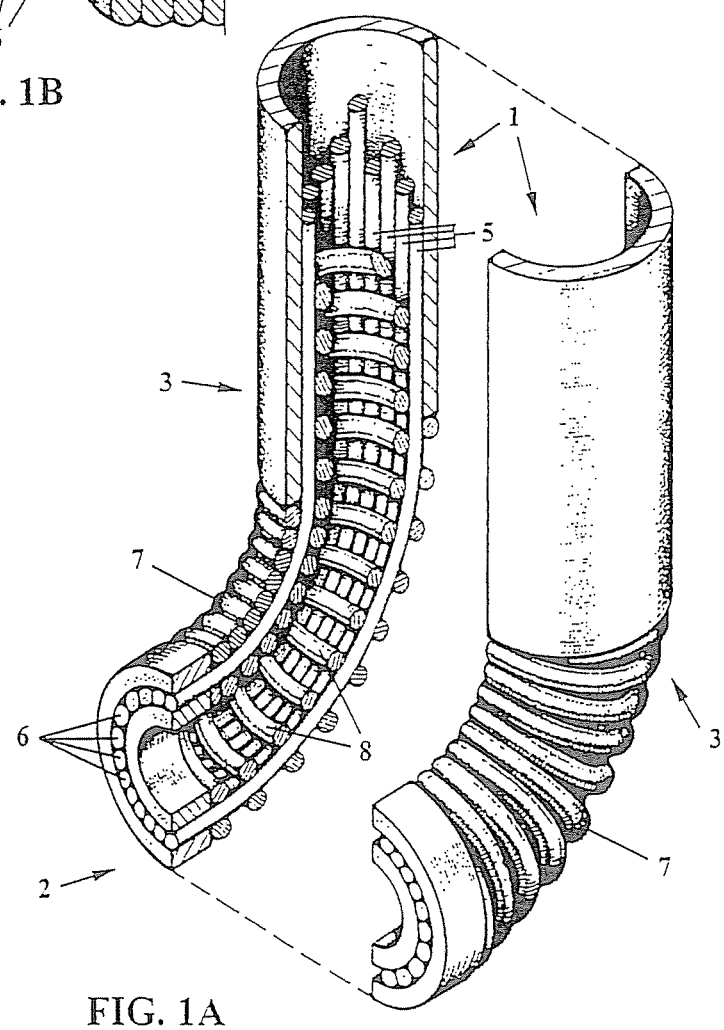
FIG. 1B
FIG. 1A

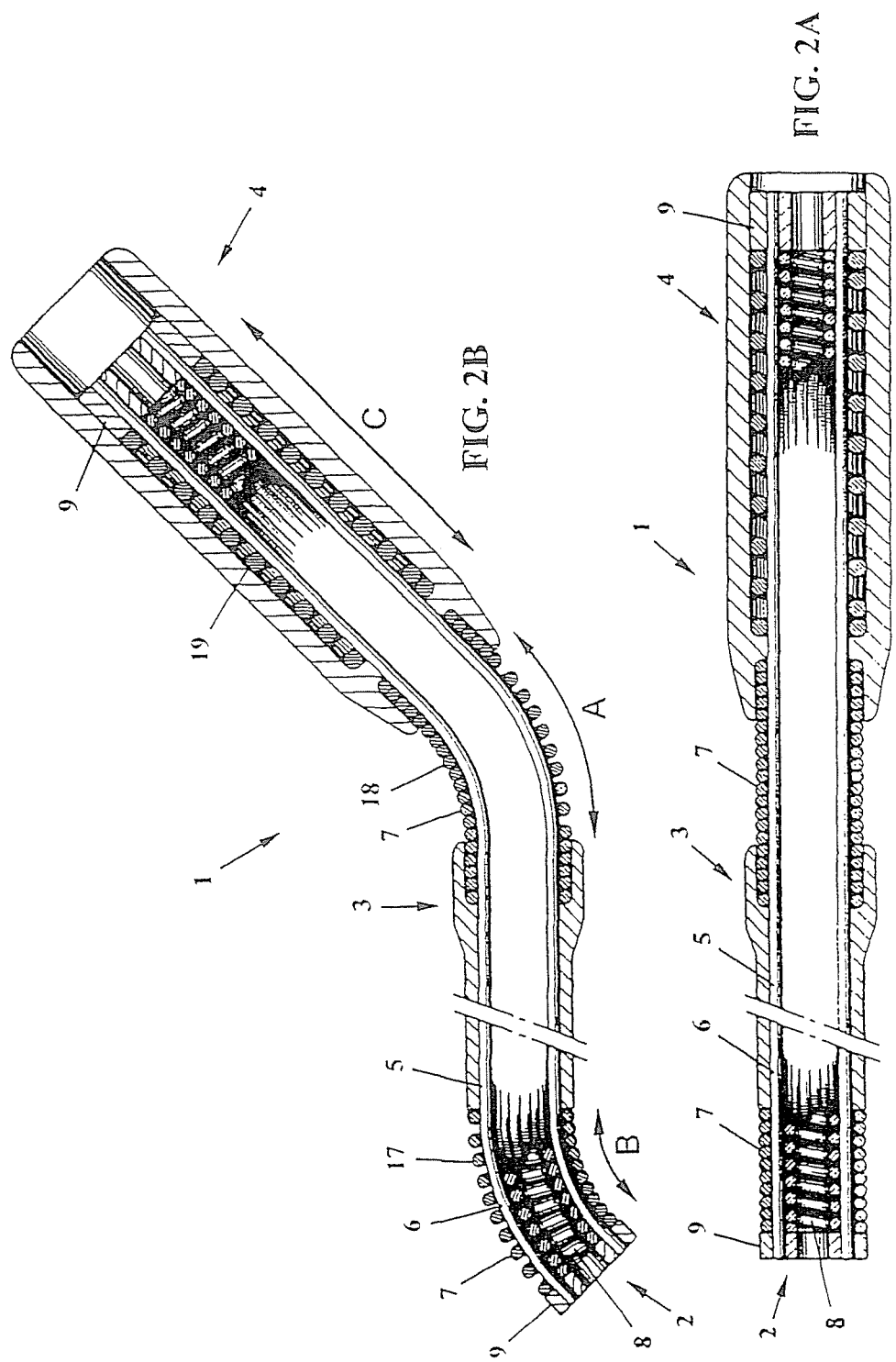

INSTRUMENT FOR FINE-MECHANICAL OR SURGICAL APPLICATIONS

The invention relates to an instrument for high-precision or surgical applications of a minimally invasive nature, comprising a distally positioned directable head, a rigid, flexible, or semi-flexible shaft upon which the head is positioned, and a proximal end equipped for operating the head. This proximal end may be provided with, or example, a handgrip or a control (possibly motor-powered). In the latter case, this may also entail a computerised control. The high-precision applications include, for example, the inspection and repair of motors, machines, radiators or tubular systems.

Such an instrument is known for medical applications from, among others, the international patent application PCT/NL01/00552, published under no. WO 02/13682.

From this publication an endoscope is known, embodied with a distally positioned camera, fitted on an endoscope shaft, wherein proximally positioned means are provided for operating the camera. To realise the coupling or the operating means and the camera, use is made of a spring, which is comprised of a chain of in themselves closed, flexible elements wherein the elements or each pair of two adjacent elements as comprised in this chain are only partially connected with each other. Through these mutually connected elements traction wires are threaded through feed-through openings that are provided in the elements.

The known construction has several drawbacks. These drawbacks concern the fact that there is a limit to how small the elements forming the spring can be while still keeping the spring at a desirably low cost price. Another drawback is that when the camera is set at an angle to the shaft, the four traction wires used in the known construction establish referred positions.

An object of the invention is to eliminate these problems and to allow the medical instrument to be constructed at low costs.

Corresponding to the preamble of claim 1, an instrument of the kind explained above is known from US-A-2002/0177750, wherein a ring of cables comprising longitudinally extending cables connects to the head, which cables are fixedly secured in the radial direction. A disadvantage of this instrument is, however, that the cables are fed through guide-sleeves provided in the longitudinal direction of the cables and attached to an externally extending leaf spring. This construction is complex and expensive.

The instrument according to the invention is characterized in that each cable of the ring of cables is disposed such that at least a part of both sides is in direct contact with another cable of the ring of cables.

This instrument lends itself especially for surgical applications, as will become apparent from the following explanation. Of course, high-precision applications are equally well possible, and may be derived without inventive effort from the explanation given hereinbelow. It should be noted that other longitudinally extending elements, with which a closed ring can be formed, also fall within the scope of the term "cable" used in the invention. This relates, for example, to a ring of (hollow) tubes, or glass fibres to be mentioned hereinbelow. Similarly, it is not necessary for all of the cables to have the same dimensions. For example, cables having a completely round cross-section may be disposed next to cables having a banana-shaped cross-section.

The instrument according to the invention can be manufactured at exceptionally low costs since the cables may be thin steel cables of the kind normally available on the market. Such steel cables are available with a diameter of, for example, 0.2 mm. This means that if a central channel delimiting the ring of cables has a diameter of 0.2 mm, it is possible to manufacture a ring of cables having a minimum diameter of 0.6 mm. It is thus possible to realise a shaft diameter having a diameter of approximately 1 mm.

An essential aspect or the invention is that in the radial and tangential direction, the cables of the ring of cables are fixedly secured. Preferably, the cables comprising the ring of cables are over their whole length in direct contact with neighbouring cables. This enables the cables of the ring of cables to absorb a pulling force as well as a pushing force, allowing the ring of cables to be used for the mechanical coupling of the head to a handgrip.

An important advantage of the instrument according to the invention is further that the same is without preferred positions with respect to the movement of the head in relation to the shaft.

For the mechanical coupling of the head to the handgrip any cable from the ring of cables may be employed. In a preferred embodiment, however, the instrument according to the invention is characterized in that the ends of at least some of the cables of the ring of cables possess a fastening to the head and to the proximal end. In this way the fastening can be constructed in a simple and consequently cheap manner, for example, by means of soldered connections or by using bolts provided in an endplate wherein the ends of the cables having a pulling function can be received.

An embodiment that is preferred when all of the cables provide the mechanical coupling for the head to the handgrip, is characterized in that the fastening is embodied as an interior ring and an exterior ring, which together delimit a slot for clampingly receiving the cables. This construction can also be used if only some of the cables of the ring or cables are received in the slot.

A simple and inexpensive embodiment of, the instrument according to the invention for the fixedly securing the ring of cables is characterized in that the ring of cables is enclosed by an exterior spring lying against the cables of the ring of cables.

It is also possible for the ring of cables to be provided at its exterior side with a construction element selected from the group comprising glass fibres, cables, power cables, power cables surrounded by glass fibres, an optionally torsion-stiff tube or tubes, optionally with lateral scoring and optionally stranded, a bellows, a stent and a spring as specified in WO 02/13682.

For the internal retention of the ring of cables numerous technical possibilities can be used. For example, a simple and effective possibility is to be found in the embodiment wherein the ring of cables is provided at its interior side with an interior spring lying against the cables of the ring of cables.

It is also possible for the ring of cables to be provided at its interior side with a construction element that is selected from the group comprising a bundle of glass fibres, a cable, power cables, a power cable surrounded by a ring of glass fibres, an optionally torsion-stiff tube or tubes, optionally with lateral scoring and optionally stranded, bellows, a stent and a spring as specified in WO 02/13682.

It is also conceivable that the construction element selected from this group is used in combination with an internal spring lying against the cables of the ring of cables. If such an internal spring is not used, the selected construction element itself must lie against the cables of the ring of cables.

If the construction element is a cable, it is advantageous that on the head of the instrument a grab jaw, scissors or clipping tongs be mounted and the cable be embodied as control cable therefor. This is especially useful for medical applications.

However, if the construction element comprises a power cable, it is advantageous for the instrument to be embodied with a camera mounted on the head, wherein the power cable serves for the power supply of said camera and/or for transporting image data obtained with the camera. Of course, it is also possible to use several power cables having separate functions. In addition, the power cable or power cables may serve for feeding a light source, such as an LED or the like. Glass fibres are also useful as light conductors, while they are at the same time able to serve as traction rope.

The instrument proposed in accordance with the invention, is preferably selected from the group comprising laparoscope, thoracoscope, colonoscope, gastroscoie, bronchoscope, endoscope, catheter, surgical drill, uretheroscope, laryngoscope, cystoscope, guidable endoscope, guidable drill, gripping tongs, clipping tongs, scissors, coagulation hook, and generally instruments for ear, nose and throat surgery, eye surgery, neurosurgery and brain surgery.

Hereinbelow the invention will be further elucidated by way of the drawing.

In the drawing:

FIG. 1a shows a cut-away drawing of substantially the head of the instrument according to the invention;

FIG. 1b shows a detail of a preferred embodiment of the fastening of the ring of cables;

FIGS. 2a and 2b show a longitudinal cross-section of an instrument according to the invention in the straight and bent condition, respectively;

Similar components in the figures carry identical reference numerals.

Figure 3:
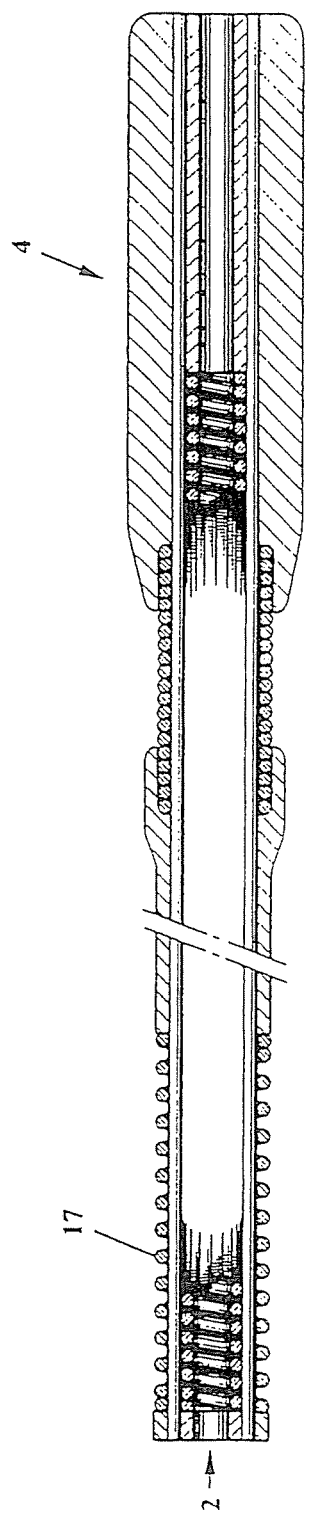
FIG. 3 shows a longitudinal cross-section or an alternative embodiment of the construction of the instrument according to the invention shown in FIGS. 2a and 2b.

With reference first to FIGS. 2a and 2b, showing the main portion of a medical instrument selected from the group comprising laparoscope, thoracoscope, colonoscope, gastroscope, bronchoscope, endoscope, catheter, surgical drill, uretheroscope, laryngoscope, cystoscope, guidable endoscope, guidable drill, gripping tongs, clipping tongs, scissors, coagulation hook, instruments for ear, nose and throat surgery, eye surgery, neurosurgery and brain surgery.

Comparison between the FIGS. 2a and 2b shows clearly that the instrument 1 possesses a distally positioned directable head 2, a shaft 3 on which a head 2 is positioned and a proximal end on which in this case a handgrip 4 is positioned that serves for controlling the head 2.

Depending on the desired application, the head 2 may be provided, for example, with a grab jaw or a camera, as will be explained hereinbelow.

A detail of the instrument 1 near the head 2 is shown in the FIGS. 1a and 1b.

FIG. 1a shows the shaft 3 and the head 2 positioned on the shaft 3 in two separate longitudinally extending halves. This illustrates that in this example shown, the shaft 3 possesses a shaft wall wherein a ring of cables 5 is contained that comprises cables 6 extending longitudinally in the shaft 3, as indicated with regard to a number of these cables in FIG. 1a. From FIG. 1a it is further clearly apparent that in the radial direction each cable 6 of the ring of cables 5 is fixedly secured. To this effect, the construction shown in FIG. 1a is provided with an external spring 7 disposed up against the cables 6 of the ring of cables 5 and an internal spring 8 lying against the interior side of the ring of cables 5 up against the cables 6 of the ring of cables 5.

The ring or cables 5 serves for the mechanical coupling of the head 2 with the handgrip 4 (see FIGS. 2a and 2b).

FIG. 1b shows an exploded view of a means for realising a fastening 9 of cables 6 of the ring of cables 5 to the head 2 and the handgrip 4, respectively. The fastening 9 shown in FIG. 1b comprises an interior ring 10 and an exterior ring 11, which together delimit a slot 12 serving to clampingly receive the cables 6 of the ring of cables 5. As already mentioned in the introduction of this exemplary embodiment, this may, for example, be realised such that only every other cable 6 is received in the slot 12. In such a case other fastenings 9 are also feasible. Some non-limiting examples are shown in FIGS. 5a and 5b.

Figure 5A:
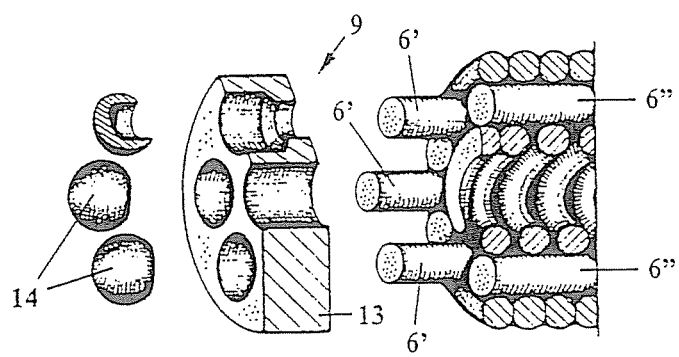
FIGS. 5a and 5b show several alternative fastenings of the cables of the ring of cables, to be used at the head and/or the proximal end of the instrument according to the invention.

FIG. 5a shows the fastening 9 wherein the ends of every other cable 6' may be received in an endplate 13 in order to be fixed therein with soldering points 14. Between these fixed cables 6' run so-called floating cables 6".

Figure 5B:
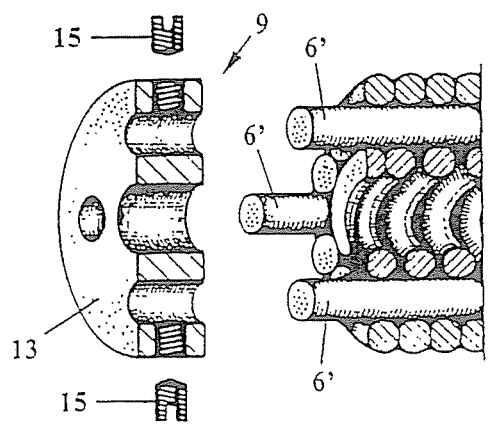

FIG. 5b shows the construction in which ends of the cables 6' are received in an endplate 13 in order to be fixed therein with bolts 15.

Figure 4:
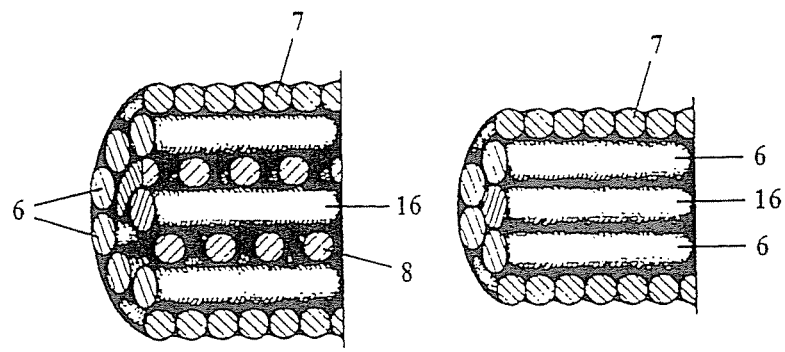
FIG. 4 shows several alternative constructions for internally securing the ring of cables forming part of the instrument according to the invention.

With respect to the interior spring 8 serving to secure the cables 6 of the ring of cables 5 at the inside, alternative embodiments are also conceivable. FIG. 4, on the right, shows an embodiment in which the cables 6 of the ring of cables are internally delimited by a cable 16. This may be, for example, a traction rope, which serves to operate a grab jaw to be mounted on the head 2 of the instrument 1. In that embodiment, the traction rope 16 is able to undergo a longitudinal movement in relation to the adjacent cables 6 of the ring of cables 5. In a manner known to the person skilled in the art, the grab jaw may be equipped with a spring element to produce a counter-force to the force to be exerted by means of the traction rope 16, such that the grab jaw can be both opened and closed, depending on the position of the traction rope 16. It should be noted, that in the construction illustrated the traction rope 16 may also be used as pushing rope, so that the said spring element may be omitted. Since a person skilled in the art is acquainted with the character of such a grab jaw, a further constructive explanation is superfluous and is therefore omitted.

FIG. 4 on the left, shows an embodiment of the instrument according to the invention wherein the traction rope 16 extends in the interior of an interior spring 8, which together with the exterior spring 7 ensures that the cables 6 of the ring of cables 5 are fixedly secured.

Apart from the just explained embodiment in which a traction rope 16 extends at the inside of the ring or cables 5, it is also possible to provide a power cable or power cables, or a power cable surrounded by a ring of glass fibres, or a tube or even a spring as specified in WO 02/13682. Another possibility is the application or a stent. Each of the above-mentioned possibilities has its advantages, which may be selected in accordance with the intended application. For example, the embodiment using the stent or using the spring known from WO 02/13682, possesses greater torsion rigidity in comparison with the embodiment using an internal spring.

The embodiment in which the construction element is a power cable, may advantageously be embodied with a camera mounted on the head 2, wherein the power cable, in a manner known to the person skilled in the art, serves to feed the camera and wherein said same cable or more additional power cables can be used for the transport of image data. It is also possible to use glass fibres, which are preferably applied in a ring around the power cable for conducting light for the image data to be recorded with the camera. The person skilled in the art is quite familiar with the manner in which this is to be accomplished, so that there is no need for further explanation.

With regard to the directability of the head 2, the working principle of the instrument 1 according to the invention may be explained quite simply by referring to the FIGS. 2a and 2b.

It is, for example, possible to fasten a miniature camera to the head 2, with a feed cable for the camera and glass fibres for the conduction of light through the interior of the interior spring 8. The cables 6 of the ring of cables 5 are fixed with a fastening 9, which at the head side surrounds the interior ring 10 discussed with reference to FIG. 1b and the exterior ring 11. A similar construction is provided at the side of the handgrip 4. The fastening 9 is at the side of the handgrip 4 slidably accommodated therein.

The illustrated instrument 1 comprises four helical springs, i.e. a compression spring 17 directly behind the head 2, a draw spring 18 between shaft 3 and handgrip 4, a compensation spring 19 accommodated in the handgrip 4 and an interior spring 8 extending over the total length of the instrument 1. It should be noted that in the (straight) shaft 3, the interior spring 8 may be substituted by a tube.

The springs have the following functions:

The draw spring 18 is embodied as closed draw spring so that the same is relatively rigid with respect to movements other than the desired bending movement. Along a portion of the circumference, the draws spring 18 is preferably glued to the shaft 3 or the handgrip 4, respectively, in order to increase the torsion rigidity of the construction.

The interior spring 8 is a weak spring whose function is to keep the cables 6 of the ring of cables 5 in position.

The function of the compensation spring 19 is to in the straight condition compress the spring 17 positioned behind the head 2 until the same is closed. To this end the compensation spring 19 is slightly heavier than the compression spring 17.

The instrument 1 works as follows: bending the handgrip 4 causes the portion of the lower cables 6 off the ring of cables 5 indicated with arrow A to elongate. Because the portion of said cables 6 indicated with arrow B is unable to shorten due to the spring 17 being in the straight condition completely closed, the cables 6 in the portion of cables 6 indicated with C are caused to shorten. This makes the fastening rings 9 in the handgrip 4 move in the direction of the distal end while the upper cables 6 are paid out to give the compression spring 17 room to bend over a same angle as draw spring 18 does as a result of the handgrip 4 being moved.

FIG. 3 finally shows a schematic illustration of an embodiment of the medical instrument 1 according to the invention, wherein she compensation spring 19 shown in FIGS. 2a and 2b in the handgrip 4 is omitted. When the handgrip 4 is being moved, the necessary length of the cables 6 must then be made available through compression of the spring 17 located behind the head 2, to which end the spring 17 must not be closed in the straight condition.

The study that resulted in the present invention was made possible by a grant from the Royal Dutch Academy of Sciences.

The invention claimed is:

1. An instrument for high-precision or surgical applications of a minimally invasive nature, comprising:
    a shaft defining a longitudinal axis and a radial direction perpendicular to the longitudinal axis; and
    a deflectable head positioned on a distal end of the shaft, wherein the shaft includes a proximal end equipped for directing the deflectable head,
    wherein the shaft is provided with a first construction element arranged internal to a ring of cables and a second construction element arranged external to said ring of cables comprising cables extending in a longitudinal direction of the shaft, the cables connected to the deflectable head and to the proximal end, wherein the cables are fixedly secured by said first and second construction elements in the shaft's radial direction and are movable in the shaft's longitudinal direction, and
    wherein each cable of the ring of cables is disposed such that at least a part of both sides of the cable is in direct contact with another cable of the ring of cables and extends parallel to the longitudinal direction of the shaft, and such that the ring of cables transmits a force from the proximal end to the deflectable head, which force causes the deflectable head to be manipulated from a position in which the deflectable head is aligned with the longitudinal axis of the shaft to a position in which the deflectable head is deflectable from the longitudinal axis of the shaft.

2. An instrument according to claim 1, wherein:
    a handgrip is positioned on the proximal end of the shaft; and
    the ring of cables is designed for mechanically coupling the deflectable head to the handgrip.

3. An instrument according to claim 2, wherein ends of at least some of the cables of the ring of cables possess a fastening to the deflectable head and to the proximal end.

4. An instrument according to claim 3, wherein the fastening is embodied as an interior ring and an exterior ring, which together delimit a slot for clampingly receiving the cables.

5. An instrument according to claim 1, wherein the second construction element is an exterior spring lying against the cables of the ring of cables.

6. An instrument according to claim 1, wherein the second construction element is provided external to the ring of cables, the second construction element selected from the group consisting of glass fibres, cables, power cables, power cables surrounded by glass fibres, a tube or tubes, bellows, a stent and a spring.

7. An instrument according to claim 1, wherein the first construction element is an interior spring provided internal to the ring of cables, the interior spring lying against the cables of the ring of cables.

8. An instrument according to claim 1, wherein the first construction element is provided internal to the ring of cables, wherein the first construction element is selected from the group consisting of a bundle of glass fibres, a cable, a power cables, a power cable surrounded by a ring of glass fibres, a tube or tubes, bellow, a stent and a spring.

9. An instrument according to claim 8, wherein the first construction element lies against the cables of the ring of cables.

10. An instrument according to claim 8, wherein the first construction element is a cable, wherein on the deflectable head a grab jaw, scissors or clipping tongs is mounted and the cable is embodied as control cable therefor.

11. An instrument according to claim 8, wherein the first construction element comprises at least one power cable, wherein a camera is mounted on the deflectable head and the power cable serves for the power supply of the camera and/or for transporting image data obtained with the camera.

12. An instrument according to claim 1, wherein the instrument is selected from the group comprising laparoscope, thoracoscope, colonoscope, gastroscope, bronchoscope, endoscope, catheter, surgical drill, uretheroscope, laryngoscope, cystoscope, guidable endoscope, guidable drill, gripping tongs, clipping tongs, scissors, coagulation hook, and generally instruments for ear, nose and throat surgery, eye surgery, neurosurgery and brain surgery.

13. An instrument according to claim 6, wherein the second construction element lies against the cables of the ring of cables.

14. An instrument according to claim 6, wherein the second construction element is a cable, wherein on the head a grab jaw, scissors or clipping tongs is mounted and the cable is embodied as control cable therefor.

15. An instrument according to claim 6, wherein the second construction element comprises at least on power cable, wherein a camera is mounted on the head and the power cable serves for the power supply of the camera and/or for transporting image data obtained with the camera.

\* \* \* \* \*